(12) United States Patent
Kawasaki et al.

(10) Patent No.: US 8,894,980 B2
(45) Date of Patent: Nov. 25, 2014

(54) WET CAKE COMPOSITION FOR COSMETIC PRODUCTS AND METHODS OF USE

(75) Inventors: Yoshiaki Kawasaki, Woodstock, CT (US); Shigeru Kishida, Storrs, CT (US); LaFrancia S. Weaver, Dayville, CT (US); Mark George LePage, Dudley, MA (US)

(73) Assignee: U.S. Cosmetics Corporation, Dayville, CT (US)

( * ) Notice: Subject to any disclaimer, the term of this patent is extended or adjusted under 35 U.S.C. 154(b) by 477 days.

(21) Appl. No.: 12/273,495

(22) Filed: Nov. 18, 2008

(65) Prior Publication Data

US 2009/0191139 A1 Jul. 30, 2009

Related U.S. Application Data

(60) Provisional application No. 60/988,998, filed on Nov. 19, 2007.

(51) Int. Cl.

| | | |
|---|---|---|
| A61K 8/00 | (2006.01) |
| A61K 8/18 | (2006.01) |
| A61K 8/25 | (2006.01) |
| A61K 8/26 | (2006.01) |
| A61K 8/27 | (2006.01) |
| A61K 8/28 | (2006.01) |
| A61K 8/29 | (2006.01) |
| A61K 8/11 | (2006.01) |
| A61K 8/19 | (2006.01) |
| A61K 8/36 | (2006.01) |
| A61K 8/44 | (2006.01) |
| A61Q 1/02 | (2006.01) |
| A61Q 1/10 | (2006.01) |

(52) U.S. Cl.
CPC ... *A61K 8/11* (2013.01); *A61K 8/19* (2013.01); *A61K 8/361* (2013.01); *A61K 8/442* (2013.01); *A61K 2800/43* (2013.01); *A61Q 1/02* (2013.01); *A61Q 1/10* (2013.01)
USPC .............................. 424/63; 424/70.7; 424/401

(58) Field of Classification Search
None
See application file for complete search history.

(56) References Cited

U.S. PATENT DOCUMENTS

| | | | |
|---|---|---|---|
| 4,268,265 A | 5/1981 | Von Wattenwyl |
| 4,606,914 A | 8/1986 | Miyoshi |
| 4,622,074 A | 11/1986 | Miyoshi et al. |
| 4,648,908 A | 3/1987 | Takasuka et al. |
| 4,755,229 A | 7/1988 | Armanini |
| 4,772,331 A | 9/1988 | Noguchi et al. |
| 5,225,112 A | 7/1993 | Miyazawa et al. |
| 5,326,392 A | 7/1994 | Miller et al. |
| 5,380,359 A | 1/1995 | Honda et al. |
| 5,458,681 A | 10/1995 | Hasegawa |
| 5,763,497 A | 6/1998 | Ikeda |
| 5,897,868 A | 4/1999 | Kobayashi |
| 6,004,541 A | 12/1999 | Avalle |
| 6,299,891 B1 | 10/2001 | Leverett |
| 6,482,441 B1 | 11/2002 | Hasegawa et al. |
| 6,582,764 B2 | 6/2003 | Fuller et al. |
| 2004/0096470 A1 | 5/2004 | Tanaka |
| 2006/0024375 A1 | 2/2006 | Hasegawa |
| 2007/0020208 A1 | 1/2007 | Gutkowski et al. |
| 2007/0089246 A1* | 4/2007 | Brun ................................. 8/405 |
| 2007/0092462 A1 | 4/2007 | Gans Russ et al. |
| 2008/0081026 A1 | 4/2008 | Tanaka |
| 2008/0081028 A1 | 4/2008 | Tanaka |
| 2008/0299158 A1* | 12/2008 | Kishida et al. ................. 424/401 |
| 2010/0203097 A1 | 8/2010 | Tanaka |

FOREIGN PATENT DOCUMENTS

| | | |
|---|---|---|
| DE | 503406 | 7/1930 |
| DE | 3142707 | 5/1983 |
| DE | 10063658 A1 | 7/2002 |
| FR | 2557123 | 6/1985 |
| FR | 2845277 A1 | 4/2004 |
| FR | 2846229 A1 | 4/2004 |
| JP | 02048510 | 2/1990 |
| JP | 06172637 | 6/1994 |
| JP | 2001-72527 A | 3/2001 |
| WO | 9415580 | 7/1994 |
| WO | 0155263 A1 | 8/2001 |
| WO | 2005056696 A2 | 6/2005 |
| WO | 2005056696 A3 | 8/2005 |
| WO | 2006136880 A1 | 12/2006 |

OTHER PUBLICATIONS

European Examination Report for European Patent Application No. 08851212.4, Mailed Feb. 10, 2012.
International Search Report and Written Opinion for PCT International Patent Application No. PCT/US2008/084039, mailed Mar. 9, 2011.
U.S. Final Office Action regarding U.S. Appl. No. 12/273,495, notification date Aug. 2, 2012.
U.S. Office Action mailed May 2, 2013 in corresponding U.S. Appl. No. 13/313,739.
Taizo Miyoshi, Ryo Ohara and Kazu Abe: Overall Review of Surface Modification Technology—Jun. 1, 2001.
International Search Report (ISR), PCT/US2008/084039, dated Jul. 15, 2003.
Ansel, Howard C. et al.; "Pharmaceutical Dosage Forms and Drug Delivery Systems" 7th edition, 1999, Lippincott Williams & Wilkins, chapters 1 & 2, pp. 1-59.
Cosmetics database CosIng entry for "Cholesteryubehenylioctyldodecyl Lauroyl Glutamate", retrieved from <http://ec.europa.eu/consumers/cosmetics/cosing> on Apr. 23, 2011, one page.

(Continued)

*Primary Examiner* — Jeffrey T Palenik
(74) *Attorney, Agent, or Firm* — Pillsbury Winthrop Shaw Pittman LLP

(57) ABSTRACT

This invention relates to water based slurry compositions of cosmetic and personal care products and methods of making and using water based slurry compositions for cosmetic and personal care products such as foundations, eye shadows, lotions, and creams.

13 Claims, 2 Drawing Sheets

(56) References Cited

OTHER PUBLICATIONS

Merriam-Webster Online Dictionary (http://www.merriam-webster.com/dictionary/suspension; downloaded Apr. 19, 2013.
Product information for "ABIL(tm) WE 09", EVONIK Industries, dated Apr. 2001, retrieved from <www.finecon.sk/admin/pdf/DS_ABIL_WE_09_e.pdf> on Apr. 23, 2011, pp. 1-5.
Schlossman, Mitchell L.;"Treated Pigments", 1990, Allured Publishing Co., Cosmetics & Toiletries, vol. 105, pp. 53-55, 58, 60 and 62-64.
U.S. Final Office Action for U.S. Appl. No. 13/313,739, notification date Aug. 8, 2013, 13 pages.
Office Action mailed Jul. 30, 2014 in Japanese Patent Application 2010-534283.

* cited by examiner

WET CAKE COMPOSITION FOR COSMETIC PRODUCTS AND METHODS OF USE

RELATED APPLICATION

This application claims priority to U.S. provisional application Ser. No. 60/988,998, filed Nov. 19, 2007, which is expressly incorporated herein by reference.

FIELD OF THE INVENTION

This invention relates to water based slurry compositions for cosmetic and personal care products and methods of making and using water based slurry compositions for cosmetic and personal care products such as foundations, eye shadows, lotions, and creams.

INTRODUCTION

Current liquid cosmetics and make-ups on market employ hydrophobic additives and ingredients, such as oils, emollients, emulsifiers, fats, hydrocarbons, waxes and paraffins to establish resistance against sebum and sweat (perspiration). Existing cosmetic and make-up products exhibit, for example, a heavy or oily feel; uneven color; short or uneven wear; low or irregular spreadability; low skin adhesion; and shade changes on the skin over time (not long lasting).

SUMMARY

This invention relates to water based slurry compositions, and methods for preparing water based slurry compositions. A water based cosmetic slurry composition includes one or more pigments and a substrate, wherein the pigment or substrate has a surface that has been chemically immobilized with at least one surface-treatment agent (e.g., hydrophobic or hydrophilic); wherein the pigment adheres to the substrate, and wherein the pigment and substrate are dispersed in a water medium. A water based cosmetic slurry composition also includes one or more pigments and a substrate, wherein the pigment or substrate has a surface that has been chemically immobilized with at least two surface-treatment agents (e.g., hydrophobic or hydrophilic); wherein the pigment adheres to the substrate, and wherein the pigment and substrate are dispersed in a water medium. A method for preparing a water based slurry composition includes providing at least one pigment and a substrate; contacting the substrate or pigment with a surface-treatment agent to produce a surface-modified substrate or pigment material, thereby producing a substrate having adhered thereto the pigment; blending the material until it is fully or partially extended, and dispersing the blended material in a liquid water based (aqueous) medium.

In various embodiments, there are two or more surface treatment agents, one or more optionally chemically immobilized onto the surface of a pigment. In particular aspects, a first or second surface treatment agent is selected form any of the surface treatment agents of formulas I to XVI in combination. In further particular aspects, a first surface-treatment agent is a compound represented by any one of Formulas I-VIII set forth herein. In additional particular aspects, a second surface-treatment agent is devoid of hydroxyl groups and alkylene oxide moieties, or is a compound represented by any one of Formulas IX-XVI set forth herein. In other additional aspects, a surface treatment agent is hydrophobic or hydrophilic, or at least one of the two surface treatment agents is hydrophobic. In still further aspects, a first surface-treatment agent has a hydrophilic-lipophilic balance of about 10 or higher (e.g., ranging from about 10 to 18 or 14 to 18) and contains at least one functional group selected from the group consisting of a carboxyl group or a salt of a carboxyl group, a phosphorous group or a salt of a phosphorous group, a sulfur group or a salt of a sulfur group, and a silane group. In yet additional aspects, a second surface-treatment agent has a hydrophilic-lipophilic balance of about 9 or lower (e.g., ranging from about 1 to 9 or 1 to 4) and contains at least one functional group selected from the group consisting of a carboxyl group or a salt of a carboxyl group, a phosphorous group or a salt of a phosphorous group, a sulfur group or a salt of a sulfur group. In such aspects, a difference in the hydrophilic-lipophilic balance values between the first and the second surface-treatment agent can be at least about 5.

In additional embodiments, a surface-treatment agent can contain one or more hydroxyl groups or alkylene oxide moieties (e.g., an ethylene oxide, propylene oxide, or a combination thereof), an acyl collagen, such as a carboxylic acid, lactate, gluconate, amino acid, acyl amino acid, fatty acid, a silane, triethoxycaprylsilane, glycerol phosphate esters, methicone, dimethicone, galacturonic acid, glucarolactone, gallic acid, glucoheptanoic acid, 12-hydroxystearic acid, laurylamidobetaine, stearyl amphoacetate, lauryl amphopropionate, stearyl amphopropionate, polyethylene, sodium myristoyl sarosinate, potassium palmitate, potassium myristate, zinc gluconate, disodium stearoyl glutamate, isostearyl sebacic acid, or a combination thereof.

In certain embodiments, a water based cosmetic slurry composition has a surface-treatment agent in an amount of about 1% to 15% by weight of the slurry. In particular aspects, a surface-treatment agent in an amount of about 1, 2, 3, 4, 5, 6, 7, 8, 9, 10, 11, 12, 13, 14 or 15% by weight of the slurry.

In certain embodiments, a water based cosmetic slurry composition has a water percentage of about 10% to 90% by weight of the slurry. In particular aspects, water percentage is greater than about 40% or 50% by weight of the slurry, or at least 60, 70%, 80%, 90%, 95% or more by weight of the slurry.

Water based slurry compositions can include additional cosmetically acceptable or compatible ingredients, in various amounts (e.g., 0.1 to 20% by weight of the slurry, or less than 20% by weight of the slurry). In particular embodiments, a water based cosmetic slurry includes a cosmetically acceptable oil, emollient, emulsifier, fat, fatty acid ester, fatty alcohol, hydrocarbon, wax or paraffin, a preservative or a fragrance.

Non-limiting classes of oils include glyceride (e.g., monoglyceride, diglyceride, triglyceride), ester (e.g., fatty acid ester, a hydroxyl acid ester), silicone or derivative thereof, a lipophilic vitamin, a hydrocarbon, a mineral oil, a castor oil derivative or a vegetable-based oil or a combination thereof. Specific examples of oils include cetyloctanoate, dimethicone, diphenyldimethicone, cyclomethicone, cetyldimethicone, polysilicone-11, caprylic- or capric-triglyceride, dimethyl polysiloxane, isostearyl neopentanoate, cetyloctanoate, diisostearyl maleate, squalane, tocopherol acetate, tocopherol (Vitamin E), retinol, retinoic acid, isododecane, isononyl isononanoate, ethylhexyl methoxycinnamate, behenyl alcohol, and cholesteryl-, behenyl-, octyldodecyl-lauroyl glutamate. Non-limiting emulsifiers include Cetyl dimethicone copolyol, Polygyceryl-4 isosteatrate, Glyceryl stearate, PEG-100 stearate, Cetyl alcohol, Dicetl phosphate, Ceteth-10 Phosphate and Isostearic acid. Non-limiting fatty acids/esters include a polyglyceryl fatty acid ester, polyalkylene glycol fatty acid ester, and polyalkylene glycol alkyl ether.

Pigments can adhere to the substrate or substrate can adhere to pigment. Pigments can be substantially uniformly distributed onto the surface of the substrate. Pigments include two or more (e.g., three, four, five or more different pigments). Pigments can be substantially deagglomerated or deflocculated. Pigments can have the same or have a different color, shade, hue, chroma (saturation) or lightness. Specific examples of pigments include a titanium dioxide, zinc oxide, zirconium oxide, zirconium dioxide, iron oxide, ultramarine, pearl pigment, manganese violet, Prussian blue, chromium oxide, chromium hydroxides, rutile, anatase, ultrafine $TiO_2$, ultrafine ZnO, yellow iron oxide, red iron oxide, brown iron oxide, black iron oxide, ultramarine blue, ultramarine violet, ultramarine pink, mica, or titanated mica. Pigments can be in an amount of less than about 70%, 60%, 50%, 40%, 30%, 20% or 10% by weight of the slurry.

Substrates include clay, mica, timron super silver, a mica coated with titanium dioxide, talc, kaolin, sericite, silica, aluminum silicate, magnesium silicate, calcium sodium silicate, fumed silica, alumino-silicate, a mineral, nylon, boron nitride, an acrylate, polymethyl methacrylate (PMMA), a metal powder, ceramic powder, cotton powder, cellulose, urethane, styrene, polyolefin, polyetheylene, polyamide, zirconium, starch and starch derivatives such as aluminum starch octenylsuccinate, or calcium carbonate (chalk).

A water based cosmetic slurry composition can be a suspension. A water based cosmetic slurry composition can be fully extended in terms of color, shade, hue, chroma (saturation) or lightness.

A water based cosmetic slurry composition can exclude certain components. In particular embodiments, a water based cosmetic slurry lacks one or more of a cosmetically acceptable oil, emollient, emulsifier, fat, fatty acid ester, fatty alcohol, hydrocarbon, wax or paraffin.

Methods for preparing and producing water based cosmetic slurry compositions are provided. In one embodiment, a method includes: providing a pigment and at least one substrate; contacting the pigment or substrate with a surface-treatment agent to produce a surface-modified pigment or substrate, thereby producing a substrate to which the pigment adheres; and dispersing the pigment and substrate in a water medium. In another embodiment, a method includes providing a pigment and at least one substrate; contacting the pigment or substrate with two surface-treatment agents to produce a surface-modified the pigment or substrate, thereby producing a substrate to which the pigment adheres; dispersing the pigment and substrate in a water medium. Surface treatment agents, pigments, substrates and other materials and amounts referenced herein in respect to water based cosmetic slurry compositions are also applicable in the preparation and production methods of water based cosmetic slurry compositions.

DETAILED DESCRIPTION

Figure 1A:
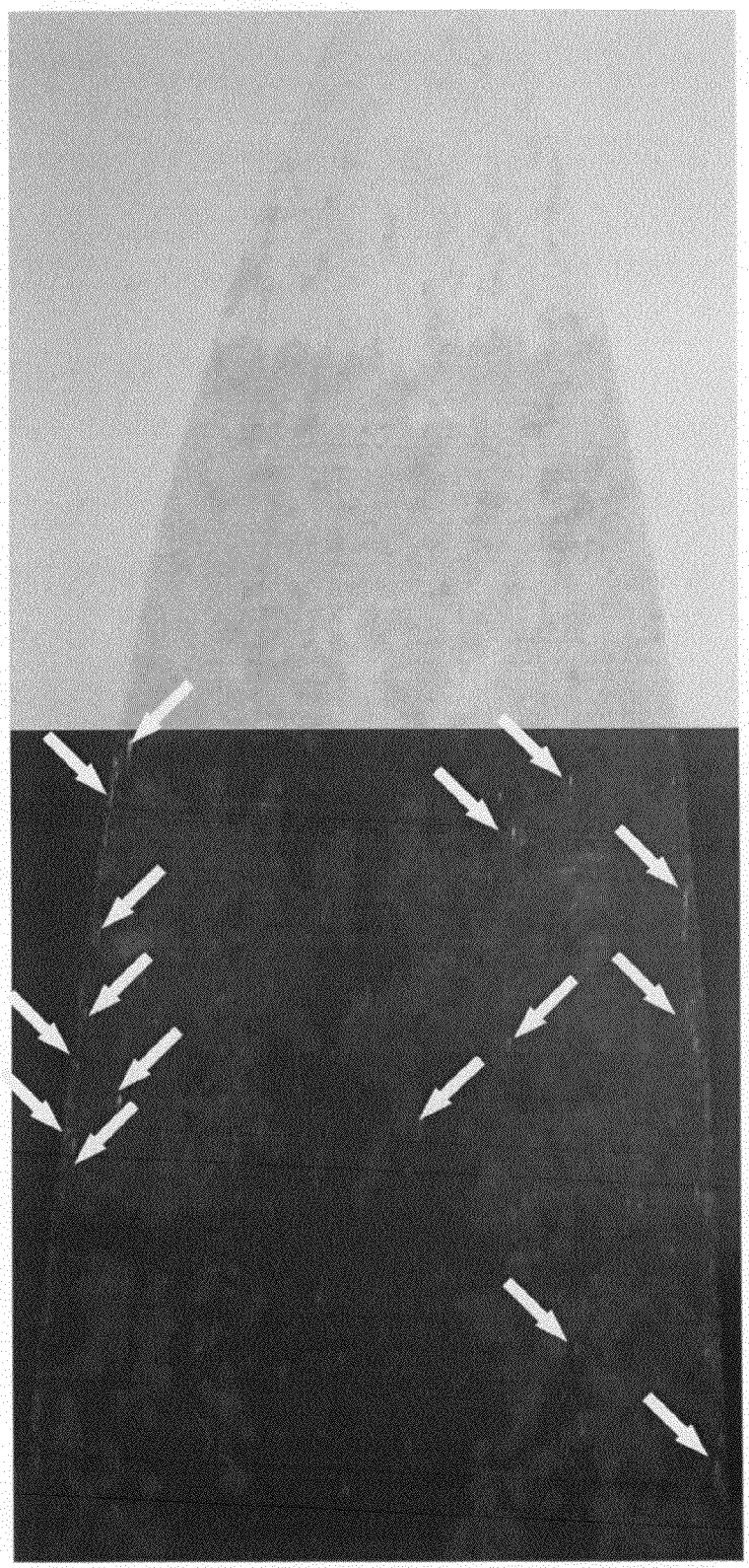
FIGS. 1A and 1B illustrate A) a conventional formulation with a white pigment (TiO2) that has numerous pigment streaks, after 5 minutes homogenizing @5000 rpm for a 200 gram batch, compared to B) a water based slurry composition and a second water based slurry composition after 2 minutes propeller mixing @500 rpm for 200 gram batch does not have streaks.

The invention provides, among other things, water based slurry compositions. Invention water based slurry compositions can be used in cosmetic and makeup products, and personal care products. Invention water based slurry compositions provide various superior properties over existing cosmetic, makeup, and personal care products. Particular non-limiting examples include a cooling or refreshing sensation or feel when applied to skin, ease of application, improved spreadability leading to less creasing on skin, ease of blending or mixing, a lighter or softer texture on skin, a lighter or softer feel or sensation when applied to skin, a more natural appearance on skin, improved and more even coverage of skin (less streaking or unevenness), longer lasting wear when applied to skin, a reduced sensation or feel of oiliness, a reduced sensation or feel of a greasy texture, retaining good skin adhesion, and sweat (perspiration) resistance and water repellancy.

A slurry is a mixture of solids in a liquid in which the solids are distributed throughout the liquid. A liquid is a smooth, amorphous substance in the fluid state of matter having no particular fixed shape (free flowing) and relatively invariable volume. A water based slurry composition typically has a single aqueous phase. Amounts of water as a percent of the weight of the slurry and in production methods can vary, but typically range from about 10% to 90%. Amounts of water as a percent of the weight of the slurry can be greater than 30%, 40%, 50%, 60%, 70%, 80%, 90%, or more. Water based slurry compositions and production methods can include an oil, emollient, emulsifier, fat, fatty acid ester, fatty alcohol, hydrocarbon, wax or paraffin, oil in water phase (o/w), water in oil phase (w/o) and water in silicone provided that one or more of the various superior properties over existing cosmetic, makeup, and personal care products are maintained (e.g., ease of application, improved spreadability leading to less creasing on skin, ease of blending or mixing, a cooling or refreshing sensation or feel when applied to skin, a lighter or softer texture on skin, a lighter or softer feel or sensation when applied to skin, etc.).

Water based slurry compositions and production methods include powder materials, which include, for example, one or more pigments and a substrate acceptable for formulation or inclusion in a cosmetic, makeup, or personal care product. A water based slurry composition and production methods can have one or more, or all pigments or substrates or other cosmetically acceptable components suitable for formulation or inclusion in a cosmetic, makeup, or personal care product.

Substrates and pigments typically comprise or consist of a material compatible or acceptable for cosmetic, makeup, and personal care products. Substrates and pigments are typically in the form of a powder, which is a solid, dry material consisting of extremely small, flowable particles. Particular classes of powder materials are inorganic and organic particles, beads, crystals, clays, metals, metal oxide powders, plastics and fillers for plastic suitable for cosmetic, makeup, and personal care product use.

Water based slurry compositions and production methods include at least one substrate and one pigment in an aqueous medium. Water based slurry compositions and production methods can include a plurality or mixture of different substrates, a plurality or mixture of different pigments, or a plurality or mixture of substrates and pigments.

Typical substrate sizes are about 1-30 microns in diameter, usually not less than 1 micron, for example, have a primary size of about 1-3 microns. Substrate particles are typically larger than pigment particles and have various shapes, for example, spherical, elliptical or "platy." Substrates provide desirable texture and other characteristics such as smoothness, silkiness, round feel, moisture feel, optical benefits (soft focusing, hiding or concealing wrinkles or blemishes), etc.

Specific non-limiting examples of substrates include clay, mica (e.g., pearl colored mica, such as Timron Super Silver™, a mica coated with titanium dioxide produced by Rona/EMD Industries), talc, kaolin, sericite, silica (e.g., silica beads such as aluminum silicate, magnesium silicate and calcium sodium silicate, Beadyl Beads™, fumed silica), alumino-silicate minerals (zeolites), nylon (e.g., nylon beads or nylon powder), acrylates such as polymethyl methacrylate (PMMA or powder), metal powders (such as aluminum), ceramic powders (such as silicon nitride or boron nitride), cotton powder, wool powder, silk powder, cellulose and cellulose powder, urethane, polystyrene and polystyrene powder, polyolefin, polyethylene and polyethylene powder, polyamide, zirconium, aluminum oxide, zirconium oxide, starch, starch powder and starch derivatives such as aluminum starch octenylsuccinate, and calcium carbonate (chalk).

Substrates include "extenders." An extender can function as a filler or bulking agent for water based slurry compositions. Extenders as a class typically have a size, shape or structure that is similar or identical to substrates as disclosed herein and understood by the skilled artisan. The term extender is typically used to refer to a substrate material that is included in a water based slurry composition but may not have a pigment adhered thereto.

Extenders include natural and synthetic substrates that may or may not have a color, shade, hue, chroma (saturation) or lightness that may vary in saturation and luminance. As with a substrate, an extender has a size typically greater than 1 micron (1 µm), for example about 1-30 microns, and can have various shapes, for example, spherical, elliptical or "platy."

Non-limiting examples of extenders include talc, kaolin (clay), natural and synthetic micas including muscovite mica and sericite, titanated mica, cotton powder, starch, magnesium carbonate, calcium carbonate, aluminum silicate, magnesium silicate, calcium silicate, synthetic silicates, clay, bentonite, montmorillionite, calcite, chalk, bismuth oxychloride, boron nitride, fumed silica, silica beads, plastic beads such as acrylics, nylons such as Nylon 12, nylon beads, aluminum, calcium, or sodium silicate, and barium sulfate.

Amounts of substrate in water based slurry compositions and preparation methods of the invention will vary depending upon the cosmetic, makeup, personal care or other product to be produced, or method of manufacture. In a water based slurry compositions weight percent of a substrate is typically about 0 to 95%.

As used herein, the term "pigment," which includes "dyes," is natural or synthetic material that has a certain color, shade, hue, chroma (saturation) or lightness. Pigments may be organic or inorganic in chemical nature. Pigments typically have a primary particle diameter not greater than about 3 microns. Pigments more typically are about one order of magnitude smaller in size than substrates, for example, about 0.1-1.0 microns in diameter. Other pigments, such as pearl pigments typically have a larger size, for example 10, 20, 30, 40, or 50-100 microns (µm).

Non-limiting examples of inorganic pigments include white titanium dioxide pigments (e.g., rutile, anatase, and ultrafine $TiO_2$), zinc oxides (e.g., ultrafine ZnO), which can be of pigment grade and have a primary size of about 0.3 µm, or ultrafine grade, and have a primary size of less than about 0.1 µm. Other inorganic pigments include zirconium oxide, zirconium dioxides, iron oxides (including yellow, red, brown, green and black iron oxides), ultramarines (such as ultramarine blue, ultramarine violet, ultramarine pink, etc.), pearl pigments (e.g., mica, titanated mica, bismuth oxychloride, etc.), manganese violet, Prussian blue, chromium oxides, chromium hydroxides, and carbon black. Non-limiting examples of organic pigments include "lake" dyes, β-carotene, carmine, chlorophyll and the like.

Water based slurry compositions and production methods include one or more different pigments. A plurality of different pigments (e.g., 2, 3, 4, 5, 6, 7, 8, 9, 10 or more pigments that optionally have a different color, shade, hue, chroma (saturation) or lightness) can be included to produce a "composite" of pigments. A plurality of different pigments, optionally having a different color, shade, hue, chroma (saturation) or lightness, can therefore be included in water based slurry compositions. Such water based slurry compositions can be conveniently referred to as "composite" slurry.

Although not wishing to be bound by theory, many pigment particles typically adhere to a substrate particle when pigment size is smaller than substrate size. In situations where pigment size is larger than substrate size, for example pearl pigments can be from about 50-100 microns in size with a platy structure, many substrate particles can adhere to a pigment particle. The term "adhere" used herein refers to either situation. Thus, the terminology "pigment adheres to the substrate" also includes "substrate adheres to the pigment."

Pigment adhered to substrate and substrate adhered to pigment show skin shades. Pigments adhered onto substrates or substrates adhered onto pigments may be uniformly (evenly) or non-uniformly (unevenly) distributed.

Amounts of pigments and dyes to employ in water based slurry compositions and production methods of the invention will vary depending upon the desired color, shade, hue, chroma (saturation) or lightness. As set forth in Example 1, pigment types, absolute amounts and relative ratios span a broad range and can be selected based upon a desired color, shade, hue, chroma (saturation) or lightness, physical (e.g., size, shape), functional or chemical characteristic or property. In water based slurry compositions and production methods, total weight percent of pigments is typically about 3 to 20%, 5 to 20%, 5 to 15%, 5 to 18% or 8 to 12%. In water based slurry compositions and production methods, total weight percent of a substrate is typically about 3 to 20%, 5 to 20%, 5 to 15%, 5 to 18% or 8 to 12%.

Ratios of pigments and substrates can also vary depending upon the cosmetic, makeup, personal care or other product to be produced, or method of manufacture. Exemplary pigment to substrate ratio in a cosmetic or makeup product is from about 5:95 to 95:5. In personal care and other products, the ratio is typically not limited.

Substrates and pigments can be deflocculated or deagglomerated. The invention therefore provides water based slurry compositions and production methods that include or employ deflocculated and/or deagglomerated substrates, pigments and other cosmetically suitable materials. Substrates, and pigments can be deflocculated or deagglomerated by any physical or chemical means which achieves at least some degree of dispersal of aggregates or agglomerates. Non-limiting examples of physical deagglomerating include shearing and grinding.

As used herein, the term "surface-treatment agent" refers to chemical agents that have the ability to modify, alter or react with the surface of a powder material (e.g., substrate or pigment) by forming chemical bonds on the surface of the powder. Specific non-limiting classes of surface treatment agents include surface active agents, which include surfactants, detergents, wetting agents and emulsifiers. Surface-active agents may be nonionic, anionic, cationic, amphoterics, hydrophobic or hydrophilic.

One or more pigments and one or more substrates are contacted with a surface-treatment agent, and the pigment or substrate is in turn either modified by the agent or the agent is bound to the surface of the pigment or substrate (e.g., absorbed, chemically linked or immobilized; see, for example, U.S. Pat. No. 5,897,868). As an example, a substrate, pigment, or a plurality of different substrates and pigments (e.g., a mixture of different colored pigments), is contacted with a surface treatment agent which in turn becomes modified by the agent or the agent is bound to surface of the substrate and/or pigment. Surface modification of substrates and/or pigments allow the material(s) present to adhere to each other.

A surface treatment agent can be chemically immobilized or adsorbed onto the surface substrate and/or pigment. Chemical linkage or immobilization of surface-treatment agents to a substrate or pigment differs from adsorption in that surface treated material has a more uniformly chemically bound reaction product. Chemical linkage or immobilization tends to reduce movement and/or rearrangement of any material linked or attached onto the surface of the modified powder material. For example, a pigment that is linked or attached to the surface of a substrate by virtue of a surface treatment agent will have less mobility than a pigment that is attached or linked to the surface of a substrate by virtue of adsorption. Chemical linkage or immobilization also differs from adding a surface active agent to the pigment or substrate in that the treated pigment or substrate typically has a uniformly chemically bound reaction product.

For chemical linkage or immobilization, the reaction may be created by a water soluble compound having a lipophilic or hydrophilic moiety absorbed onto pigment or substrate surface. With the addition of a water soluble salt of a polyvalent metal for example, a chemical bond can be produced. The reaction product provides a chemical immobilized treatment onto the surface of the particles of the pigment or substrate, or a chemically immobilized pigment or substrate surface treatment. In contrast, a simple coating of a surface active agent absent chemical immobilization renders it a free-flowing, unreliable, and inadequate functional layer which is only absorbed onto the surface of the pigment or substrate. Surface treatment agents can be chemically linked or immobilized onto the surface of a pigment or substrate by methods known in the art (e.g., U.S. Pat. No. 5,897,868).

In order to facilitate or enhance linkage or immobilization of surface-treatment agents to substrate or pigment, a reaction may be created by a water soluble compound having a lipophilic or hydrophilic moiety being absorbed onto the surface of the substrate or pigment. As a non-limiting example, addition of a water-soluble salt of a polyvalent metal, such as magnesium, calcium, barium, aluminum, titanium, zinc or a zirconium salt (e.g., zirconium sulfate or chloride), or an alkaline salt, such as a sodium, potassium, lithium, ammonium, or an amine salt, can produce a chemical linkage. The reaction provides a surface-treatment agent chemically immobilized onto the surface of the substrate or pigment particle. In contrast, coating a substrate or pigment with a surface-treatment agent involves absorbing the surface-treatment agent onto the surface of the substrate or pigment.

Surface-treatment agents typically have one or more reactive groups, such as a hydrophilic moiety (e.g., a carboxyl group, a phosphorous group, a sulfur group, a silanol group or a silane group) or a hydrophobic moiety (e.g., a hydrocarbon, a dialkyl($CH_3$—, $C_2H_5$—) polysiloxane, perfluoroalkyl, etc.) in their structure. Surface-treatment agents may or may not contain one or more hydroxyl groups or alkylene oxide moieties, such as ethylene oxide or propylene oxide. Those having hydroxy groups in their structure and hydrophilic characteristics can be delivered after completing the reaction onto the surface. Where there are two or more surface-treatment agents (e.g., first, second, third, fourth, fifth, etc., surface-treatment agents), the surface treatment agents can have a hydrophilic moiety (e.g., two, three, four, five, etc., or more, hydrophilic moieties), a hydrophobic moiety (e.g., two, three, four, five, etc., or more, hydrophobic moieties), or a combination of a hydrophilic moiety and a hydrophobic moiety (e.g., one hydrophilic moiety and a hydrophobic moiety, two hydrophilic moieties and one hydrophobic moiety, two hydrophobic moieties and one hydrophilic moiety, three hydrophilic moieties and one hydrophobic moiety, two hydrophilic moieties and two hydrophobic moieties, three hydrophobic moieties and one hydrophilic moiety, etc.). A first or second surface-treatment agents can be devoid of one or more hydroxyl groups and/or alkylene oxide moieties.

Non-limiting examples of surface treatment agents include acyl collagens, ether carboxylic acids, lactates (e.g., lactic acid), gluconates (e.g., gluconic acid), galacturonic acid, glucarolactone, gallic acid, glucoheptanoic acid, amino acids (such as thereonine and serine) and their salts, acyl amino acids (such as acylglutamates, acylsarcosinates, acylglycinates, and acylalaninates), silanes, 12-hydroxystearic acid, laurylamidobetane, stearyl amphoacetate, lauryl amphopropionate, stearyl amphopropionate, fatty acids and their salts, glycerol phosphate esters (such as lecithin) and polyethylenes with free carboxylic acids.

Examples of anionic surface treatment agents (surfactants) include soaps (fatty acids/alkyl carboxylic acids salt), hydroxy fatty acids, alkyl sulfate, alkyl ether phosphate, polyoxyalkylene alkyl ether sulfate, polyoxyalkylene alkyl ether carboxylate, alkylether phosphate, acyl N-methyl taurate, N-acylamino acid salts (glutamate, sarcosinate, alaninate, glycinate, β-alaninate), acyl peptides (acyl collagen, acyl silk protein), sodium cocoate, stearic acid, iso-stearic acid, potassium palmitate, sodium laurate, 12-hydroxystearic acid, sodium lauryl sulfate, sodium myristyl phosphate, sodium myristoyl sarcosinate, sodium polyoxyethylene lauryl sulfate, polyoxyethylene myristyl carboxylate, potassium myristate, zinc gluconate, isostearyl sebacic acid, sodium myristoyl taurate, disodium stearoyl glutamate, disodium cocoyl glutamate, arginine lauryl glycinate, sodium dilauramidoglutamide lysine.

Exemplary surface treatment agents, with moieties representing hydrophilic characteristics, include structures and salts of [Formulas I-VIII]:

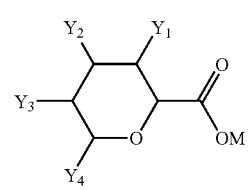

[Formula I]

Wherein,

Y1, Y2, Y3 and Y4 are independently selected from hydrogen, hydroxy group, alkoxy group or oxo group, and at least one of Y1, Y2, Y3, or Y4 is a hydroxy group; and M is either hydrogen, or metal or its equivalent (organic base such as triethanolamine, aminomethyl propanol, lysine, etc.).

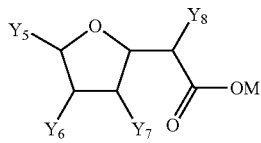
[Formula II]

Wherein,
Y5, Y6, Y7 and Y8 are independently selected from hydrogen, hydroxy group, alkoxy group or oxo group, and at least one of these is a hydroxy group; and
M is either hydrogen, or metal or its equivalent (organic base such as triethanolamine, aminomethyl propanol, lysine, etc.)

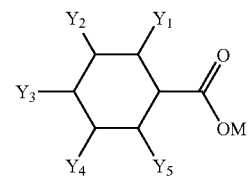
[Formula III]

Wherein,
Y1, Y2, Y3, Y4 and Y5 are independently selected from hydrogen, hydroxy group, alkoxy group or oxo group, and at least one of these is a hydroxy group; and
M is hydrogen, or metal or its equivalent (organic base such as triethanolamine, aminomethyl propanol, lysine, etc.).

A specific non-limiting example of a Formula III surface-treatment agent is Gallic acid.

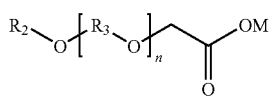
[Formula IV]

Wherein,
R2 is an alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group;
R2 has 8 to 12 carbons (C8~C24);
R3 is ethylene, propylene, or butylene;
n is an integer from 1 to 60; and
M is hydrogen, or metal or its equivalent (organic base such as triethanolamine, aminomethyl propanol, lysine, etc.).

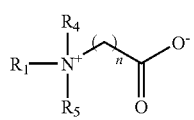
[Formula V]

Wherein,
R1, R4 and R5 are independently an alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group;
Or R1, R4 and R5 have 1 to 24 carbons (C1~C24); and
n is an integer from 1 to 24.

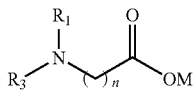
[Formula VI]

Wherein,
R1 and R3 are independently an alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group;
R1 and R3 is 1 to 24 carbons (C1~C24);
n is an integer from 1 to 24; and
M is hydrogen, or metal or its equivalent (organic base such as triethanolamine, aminomethyl propanol, lysine, etc.).

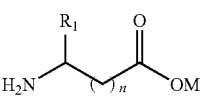
[Formula VII]

Wherein,
R1 is independently an alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group;
R1 and R3 is 1 to 24 carbons (C1~C24);
n is an integer from 1 to 24; and
M is hydrogen, or metal or its equivalent (organic base such as triethanolamine, aminomethyl propanol, lysine, etc.).

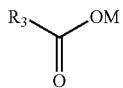
[Formula VIII]

Wherein,
R1 is an alkyl, alkylamide, alkenyl, alkynyl, alkoxy, aryl, cycloalkyl, arylalkyl group, all of which may be substituted by at least one or more hydroxy group, and may further be substituted by one or more hydroxy, alkoxyl, carboxyl, or oxo group;
R1 is 8 to 24 carbons (C8~C24); and
M is hydrogen, or metal or its equivalent (organic base such as triethanolamine, aminomethyl propanol, lysine, etc.).

Exemplary surface treatment agents, with moieties representing hydrophobic characteristics, include structures and salts of Formulas IX-XVI:

[Formula IX]

Wherein,
R3 is an alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group;
R3 is 8 to 24 carbons (C8~C24); and
M is hydrogen, or metal or its equivalent (organic base such as triethanolamine, aminomethyl propanol, lysine, etc.).

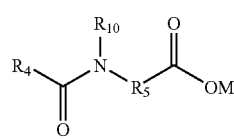

acylamino acids and their salts,

Wherein,

R4 and R5 are each independently alkyl, alkylamide, alkenyl, alkynyl, alkoxy, aryl, cycloalkyl, arylalkyl, amino acid group, all of which may be substituted by one or more hydroxy group, and may further be substituted by one or more alkoxyl, carboxyl, or oxo group;

R4 is 8 to 24 carbons (C8~C24);

R10 is hydrogen or methyl; and

M is hydrogen, or metal or its equivalent (organic base such as triethanolamine, aminomethyl propanol, lysine, etc.).

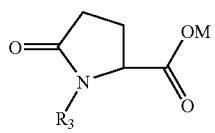

Wherein,

R3 is an alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group;

Or R3 is 8 to 24 carbons (C8~C24); and

M is hydrogen, or metal or its equivalent (organic base such as triethanolamine, aminomethyl propanol, lysine, etc.).

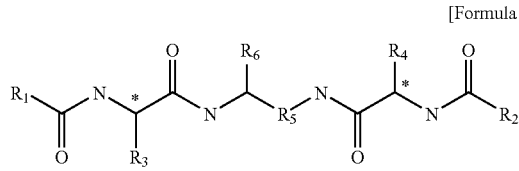

Wherein,

R1 and R2 is an alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group;

R1 and R2 are each independently 8 to 24 carbons (C8~C24);

R3 and R4 are amino acid residual moieties;

R5 and R6 are an alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group; and at least one of R3, R4 and R6 has a carboxylic group, of which structure is either an acid form or a salt form, which is a metal, such as sodium, potassium, etc. or its equivalent; organic base such as triethanolamine, aminomethyl propanol, lysine, etc.

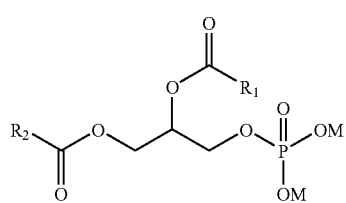

Wherein,

R1 and R2 are each independently alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group;

Or R1 and R2 are each independently 8 to 24 carbons (C8~C24); and

M is hydrogen, or metal or its equivalent (organic base such as triethanolamine, aminomethyl propanol, lysine, etc.).

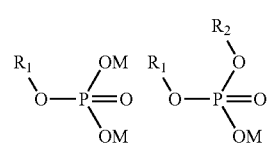

Wherein,

R1 and R2 are each independently alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group;

Or R1 and R2 are each independently 8 to 24 carbons (C8~C24); and

M is hydrogen, or metal or its equivalent (organic base such as triethanolamine, aminomethyl propanol, lysine, etc.).

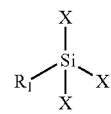

Wherein,

R1 is an alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group;

Or R1 is 8 to 24 carbons (C8~C24); and

X is an alkoxy (e.g., methoxy, ethoxy, isopropoxy, isobutoxy, etc.) or a halogen (Cl, Br, etc.)

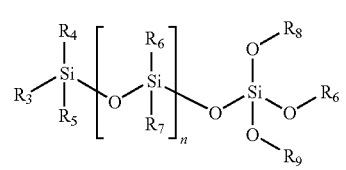

Wherein, $R_3$, $R_4$, $R_5$, $R_6$, $R_7$, $R_8$, and $R_9$ are each independently an alkyl, alkyl amide, alkenyl, alkylnyl, alkoxy, aryl, cycloalkyl, or arylalkyl group, all of which may be substituted by one or more hydroxyl, alkyoxyl, carboxyl, or oxo groups; and n is an integer from 1 to 60.

Substituent M in a compound can represent either a hydrogen or a metal or its equivalent. When M is a hydrogen, a carboxyl group forms and is thus present on the compound; when representing a metal or its equivalent, the salt of a carboxyl group forms and is thus present in the compound. Like any salt, a metal or equivalent retains an overall positive charge and the oxygen retains an overall negative charge. Exemplary metals include sodium, potassium, calcium, aluminum, and zinc; metal equivalents include amines such as monoethanolamine, diethanolamine, triethanolamine and ammonium, and organic bases such as lysine and arginine.

Alkyl, alkyl amide, alkenyl, alkylnyl, and alkoxy, groups as substituents set forth herein can be based upon alkyl groups having, for example, 1-24 carbon atoms. Such substituents can be fewer, for example, 1-20, 1-16, 1-12, 1-6 carbon atoms; such as aryl, cycloalkyl, and arylalkyl groups containing 6-24 carbon atoms, or fewer, e.g., 6-10 carbon atoms.

In particular embodiments in which there are two or more surface treatment agents, each of which are optionally chemically immobilized onto the surface of a pigment, the first and the second surface treatment agent can be selected form any of the surface treatment agents set forth herein. Thus, for example, a first and a second surface treatment agent can be any of formulas I to XVI in any combination.

In additional particular embodiments in which there are two or more surface treatment agents, one or more optionally chemically immobilized onto the surface of a pigment, a first and second surface treatment agent can have a relatively high hydrophilic-lipophilic balance (HLB) and a second surface treatment agent can have a relatively low HLB. In an exemplary embodiment, a first surface-treatment agent has a hydrophilic-lipophilic balance of about 10 or higher (e.g., 11, 12, 13, 14, 15, 16, 17, 18, etc.) and contains at least one functional group selected from the group consisting of a carboxyl group or a salt of a carboxyl group, a phosphorous group or a salt of a phosphorous group, a sulfur group or a salt of a sulfur group, and a silane group; and a second surface-treatment agent has a hydrophilic-lipophilic balance of about 9 or lower (e.g., 8, 7, 6, 5, 4, 3, etc.) and contains at least one functional group; and the difference in the hydrophilic-lipophilic balance values between the first and the second surface-treatment agent is at least about 5 (e.g., 6, 7, 8, 9, 10, 11, 12, 13, 14, 15, 16, 17, 18, 19, etc.). In various aspects, a functional group is selected from a carboxyl group or a salt of a carboxyl group, a phosphorous group or a salt of a phosphorous group, a sulfur group or a salt of a sulfur group. In another embodiment, a first surface-treatment agent has a hydrophilic-lipophilic balance ranging from about 14 to 18. In an additional embodiment, a second surface-treatment agent has a hydrophilic-lipophilic balance ranging from about 1 to 4. In particular aspects, a first surface-treatment agent contains one or more hydroxyl groups or alkylene oxide moieties (e.g., an ethylene oxide moiety, a propylene oxide moiety, or a combination thereof).

When high hydrophilic-lipophilic balance (HLB) and low HLB of surface treatment agents are employed, a pigment or substrate is imparted with the functionalities of both surface treatment agents. A surface treatment agent with a relatively low HLB imparts hydrophobic properties onto the pigment surface that may prevent the pigment from exhibiting the degradation properties associated with the pigment's inherently strong hydrophilic properties, such as fading and/or discoloration when contacted with sweat or perspiration. A surface treatment agent with a relatively high HLB imparts hydrophilic properties onto the pigment or substrate surface so that the pigment or substrate can disperse in a water-based cosmetic slurry composition with minimal addition of emulsifiers. Unlike conventional emulsifiers added after the pigment or substrate has been surface treated, both surface treatment agents can therefore act in a manner sufficient to disperse the pigment or substrate in a water-based cosmetic slurry composition. Thus, there is little or no need for additional emulsifiers after the pigment or substrate has been treated because the surface-modified pigment or substrate, when modified with the two types of surface treatment agents, can self emulsify.

If desired, additional surface-treatment agents may also be added. For example, more than one hydrophilic surface treatment agent and more than one hydrophobic surface treatment agent may be used. Additional surface treatment agents can be adhered to the pigment or substrate to impart additional functionality of these surface treatment agents. The additional surface treatment agents need not be within the genera of first and second surface treatment agents described herein.

Amounts of a surface treatment agent to employ in water based slurry compositions and production methods of the invention will vary depending upon the cosmetic, makeup, personal care or other product to be produced, or method of manufacture. For example, a surface-treatment agent may be used in an amount of at least 0.1% by weight (wt %), based on the weight of the powder material. Surface-treatment agents are typically present in an amount ranging from about 1.0 to about 200% by weight; or, from about 1.0 to about 60% by weight; or, from about 3.0 to about 30% by weight; or from about 5.0 to about 20%. Relatively low amounts of surface-treatment agents can also be used, e.g., 5.0%, 4.0%, 3.0% or less.

The amount of a surface-treatment agent can depend, at least in part, on the specific surface area of target pigment(s), extender(s) and substrate(s). For example, for regular iron oxide pigments, 2 to about 10 parts by weight of surface-treatment agent per 100 parts of powder. For an ultrafine powder, such as silica having a large surface area, 15 to about 100 parts by weight per 100 parts of powder. Thus, the greater the surface area, the more surface-treatment agent used.

In a particular non-limiting example, for a mixture of one or more pigments with one or more substrates, a surface treatment agent is in an amount of about 0.5 to 400 parts per 100 parts of pigment and substrate. In a particular non-limiting example of a water based slurry composition, the weight percent of a surface treatment agent, based upon the total weight of the pigment(s)+substrate(s) is typically about 0.5 to 20%, or about 1.0 to 15%.

During treatment with a surface treatment agent, surface of one or more substrate(s) or pigment(s) become modified and in turn particles of the substrate or pigment adhere to each other. For example, small pigment particles become attached or linked to larger particles, such as substrate particles. Including a cosmetically acceptable oil (a single oil or mixture of oils) during a treatment in which substrate or pigment surface is hydrophobically modified invites oil at the same time as the particles to become attached or linked to each other. Surface treatment agents and oil in combination function as a "glue" to attach or link particles, and other components optionally present, to each other. A mixture of two or more different pigments during such surface treatment results in forming color pigment composites, which are typically randomly and uniformly distributed onto the surface.

Prior to or following surface treatment the material can be admixed or blended with another (e.g., second) powder material, such as a different pigment, or substrate or extender, or another cosmetically acceptable ingredient such as an oil, emulsifier, emollient, fat, wax, paraffin, etc. Other components such as oils, emulsifiers emollients, fats, waxes and paraffins, etc., can therefore be present in a mixture with one or more substrates and pigments before during or after contact with a surface treatment agent. The second material may or may not have been treated with a surface treatment agent. Alternatively, two or more materials (e.g., different colored pigments), can be combined or mixed together prior to contact with a surface treatment agent, and then subsequently contacted with a surface treatment agent in order to simultaneously produce two or more surface modified or coated materials.

Oils, emollients, emulsifiers, fats, hydrocarbons, waxes and paraffins can be included in water based slurry composition and production methods. For example, an oil (emollient) may but need not be present during surface treatment of a powder material such as pigment(s) or substrate(s). An oil may but need not be added prior to, during or following surface treatment of a pigment or substrate. A water based slurry composition may therefore include a binder such as an oil, if desired. A binder such as an oil may but need not be added prior to or after making a water based slurry composition.

"Binders" in color cosmetic industry typically refer to compounds that provide adhesive properties to material such as substrates and pigments so they remain together. Binders include oils, emulsifier, emollients, fats, fatty acids, fatty acid esters, fatty alcohols, hydrocarbons, waxes, paraffins, such as metal soaps as a solid binder (e.g., zinc stearate, magnesium palmitate, etc.), latex emulsions, styrene, styrene butadiene, polyvinyl acetate (PVA), acrylic, acrylic-styrene, acrylic polyvinyl acetate, poylurethanes, and others acceptable for cosmetic, makeup, and personal care products.

Amounts of a binders in a water based slurry composition and production methods of the invention will vary. In a non-limiting example, the weight percent of binders is typically about 0 to 25%. Binders may be used in an amount of about 0.1 to 20% by weight, and are typically present in an amount less than 20% by weight of slurry.

Oils include esters and waxes such as glycerides (e.g., monoglycerides, diglycerides and triglycerides), fatty acid esters (polyglyceryl acid ester, polyalkylene glycol fatty acid ester, polyalkylene glycol alkyl ether), hydroxyl acid esters, dimer acid esters, other naturally derived esters (such as castor oil derivatives and vegetable-based oils, such as vegetable squalane), olive oil, camellia oil, macadamia nut oil, castor oil. Wax esters include esters of higher fatty acids and higher fatty alcohols, carnauba wax, candelilla wax, jojoba oil, bees wax, lanolin. Fatty esters include isopropyl myristate, isononyl isononanoate, octyldodecyl myristate, cetyl octanoate, diisostearyl malate, caprylic- and capric triglyceride, isodecyl neopentaoate, isosteraryl neopentanoate, and cholesteryl-behenyl-, octyldodecyl-lauroyl glutamate. Petroleum and synthetic oils include hydrocarbons such as paraffins, isoparaffin, petrolatum, ceresin, microcrystalline wax, squalane; silicones and derivatives thereof (such as methicone, dimethicone, cyclomethicone, cetyldimethicone, diphenyldimethicone, polysilicone-11, etc.), lipophilic vitamins and their derivatives (tocopherol, tocopherol acetate, tocopherol succinate, retinol, retinoic acid, retinyl parmitate, ascorbyl parmitate, etc.), lipophilic dyes, essential oils, and combinations thereof. Higher fatty acids include lauric acid, myristic acid, palmitic acid, stearic acid, isostearic acid, behenic acid, oleic acid, linoleic acid, linolenic acid, ricinoleic acid, docosa-polyenoic acid, erucic acid. Higher alcohols include behenyl alcohol, cetyl alcohol, stearyl alcohol, isostearyl alcohol, octyldodecanol. Oils also include silicones: dimethyl polysiloxane ("dimethicone," available as DC 200 from Dow Corning), methylphenyl polysiloxane, cyclopentasiloxane, cetyl dimethicone, and PEG/PPG dimethicone. Other oils include mineral oil, isostearyl neopentanoate, caprylic/capric triglyceride, cetyloctanoate, diisostearyl maleate, isododecane, isononyl isononanoate, ethylhexyl methoxycinnamate, behenyl alcohol, and cholesteryl-, behenyl-, octyldodecyl-lauroyl glutamate. Choosing a particular oil depends in part on the product being produced.

Oil can be applied as a liquid. Oils that are not commercially available as liquids, such as ascorbyl palmitate, which is lipophilic vitamin and sold primarily as a solid, can be solubilized in liquid oil before being used as a coating oil. Suitable solubilizing oils include vitamin E acetate, caprylic/capric triglyceride, and others. Once in a liquid form, the oil may then be added to the material using conventional techniques. For example, the oil may be poured into an intake port during and mixed until the composition is homogeneous.

Oil, when present, is typically in an amount ranging from about 0.1 to 20% by weight, based on the weight of the substrate/pigment material. Oil, when present, can be in an amount ranging from about 1.0 to about 10% by weight; or, from about 3.0 to about 5.0% by weight. Oil can be less than 20%, 15%, 10%, 5%, or less, or absent. The combined weight percentage of a surface-treatment agent(s) and oil, if oil is present, is typically less than about 5.0% by weight, based on the weight of the material. Typically, a combined weight percentage ranges from about 2.0 to about 4.0%; or, from about 4.0 to about 20% by weight; or, from about 5.0 to about 50% by weight or, from about 5.0 to about 100% by weight or, from about 5 to about 200% by weight.

Emulsifiers, surfactants, dispersants, suspending agents, emulsion stabilizers, defoamers, thickeners and other cosmetically acceptable materials and agents can also be employed in the water based slurry composition and production methods. Non-limiting examples of emulsifiers include cetyl dimethicone copolyol, polygyceryl-4 isosteatrate, glyceryl stearate, PEG-100 stearate, cetyl alcohol, dicetl phosphate, and ceteth-10 phosphate isostearic acid.

Surfactants typically include nonionic forms. Non-limiting examples of nonionic surfactants include polyoxyalkylene (PEG or/and PPG) type nonionic emulsifiers having structures:

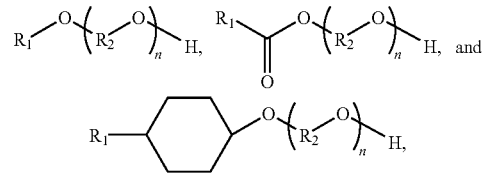

wherein $R_1$ is selected from the group consisting of alkyl, alkylamide, alkenyl, alkynyl, alkoxy, aryl, cycloalkyl, and arylalkyl group, each of which may be substituted by one or more hydroxy group, and may further be substituted by one or more alkoxyl, carboxyl, or oxo group. $R_1$ has a carbon number of $C_8$ to about $C_{24}$; $R_2$ is selected from the group consisting of $-C_2H_4-$, $-C_3H_6-$, and $-C_4H_8-$.

Further non-limiting examples of nonionic surfactants include polyhydric alcohol ester type emulsifiers wherein at least one of the hydroxy group (—OH) of a "polyol" is esterified with a fatty acid, leaving residual hydroxy groups to function as hydrophilic moieties. Residual hydroxy groups can also be modified by alkylene oxide at different polymerization number. The combination of esterified (hydrophobic) and free hydroxyl (hydrophilic) groups allows the surfactant molecule to act as an emulsifier. Non-limiting examples of polyols having different numbers of hydroxyl groups include glycerine with 3 —OH's; pentaerythritol and sorbitan each with 4 —OH's; sorbitol with 6 —OH's; and sucrose with 8 —OH's. Additional non-limiting examples are shown below:

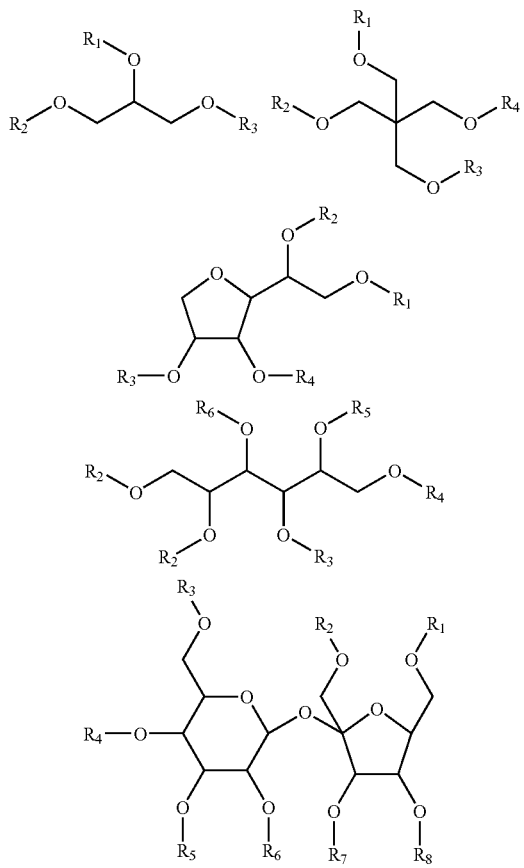

wherein $R_1$, $R_2$, $R_3$, $R_4$, $R_5$, $R_6$, $R_7$ and $R_8$ are each independently a moiety of "structure I" or "structure II" and at least one of $R_1$, $R_2$, $R_3$, $R_4$, $R_5$, $R_6$, $R_7$ and $R_8$ is "structure I".

Structure I

R: alkyl, alkenyl, alkynyl, ...
C8~C24

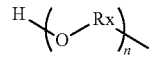

Stucture II

Rx:   —C2H4—,   —C3H6—,   or   —C4H8—
n = 0~60

Figure 1B:
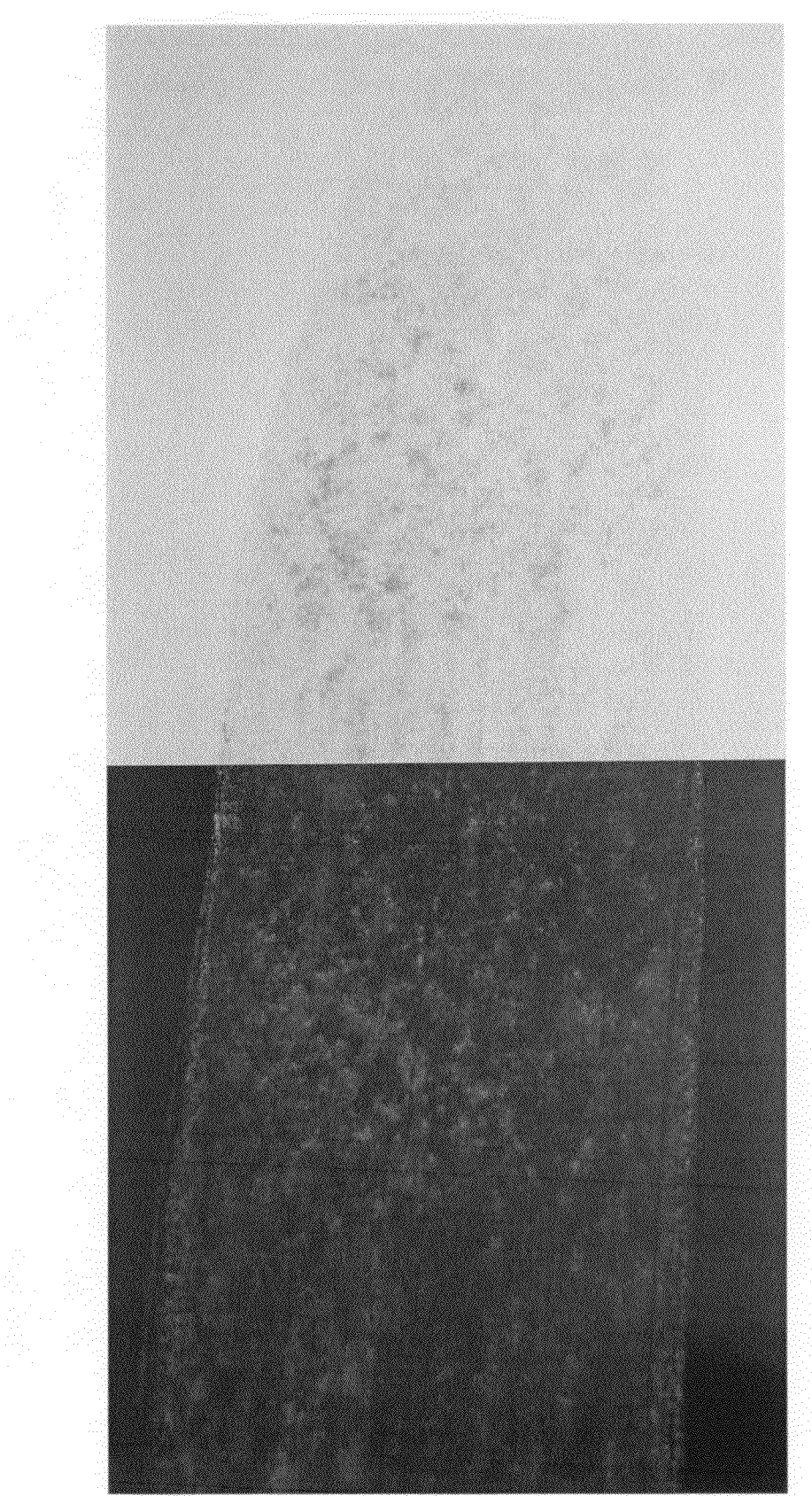

Water based slurry compositions and production methods can be fully extended. The term "fully extended," when used in reference to a water based slurry composition means that when mixed with a second slurry composition to adjust the shade or color of the slurry, the two slurry compositions are rapidly blended with little or no streaking of the color or shade of the slurry mixture. Thus, a water based slurry composition can exhibit no streaks after a relatively short time or gentle mixing and does not require extended mixing or blending time or high rates of mixing speeds to provide a substantially uniform or homogeneous color, shade, hue, chroma (saturation) or lightness. In a particular embodiment, blending of a slurry composition can occur in 1 minute or less at 600 rpm for a 200 gram batch without color or shade streaks. In further embodiments, blending of a slurry composition can occur in 10 minutes or less at 600 rpm for a 200 gram batch without color or shade streaks; in 5 minutes or less at 600 rpm for a 200 gram batch; or in 2 minutes or less at 600 rpm for a 200 gram batch. The color of any streaks will depend upon the shade blended. Thus, for a red shade, the streaks, if present, will appear red, for a yellow shade, streaks, if present, will appear yellow, for a white (light) shade, streaks, if present, will appear white (light), and for a black or dark shade, streaks, if present, will appear black or dark. As illustrated in FIG. 1A, a water based slurry composition mixed with a second water based slurry composition for 2 minutes at 500 rpm in a 200 gram batch does not form streaks. In contrast, shade adjustment of a conventional formulation with a white pigment (TiO2) reveals the presence of numerous pigment streaks after 5 minutes of homogenization at 5000 rpm for a 200 gram batch (FIG. 1B).

The rapid and easy blendability of water based slurry compositions without streaks, Example 1 (shown in Table 2) blended with Example 10 (shown in Table 9) to form Example 16, compared to conventional formulations, Comparative Examples 4-6 blended with two different red iron oxides, is illustrated in Table 1:

TABLE 1

| | | Example 16 | Comparative Example 4 | Comparative Example 5 | Comparative Example 6 |
|---|---|---|---|---|---|
| Starting Foundation Formula | Example 1 (Table 2) | 97.50 | — | — | — |
| | Comparative Example 1 (Table 3) | — | 100.00 | — | — |
| | Comparative Example 2 (Table 4) | — | — | 100.00 | — |
| | Comparative Example 3 (Table 5) | — | — | — | 100.00 |
| Shade adjustment | Example 10 (Table 9) | 2.50 | — | — | — |
| | Red iron oxide, Disodium Stearoyl Glutamate | — | 0.15 | 0.15 | — |
| | Red Iron Oxide, Potassium Myristate | — | — | — | 0.15 |
| Propeller/ scraper mixer @ 600 rpm | 1 minutes | No streaks | Streaks | Streaks | Streaks |
| | 2 minutes | No streaks | Streaks | Streaks | Streaks |
| | 5 minutes | No streaks | Streaks | Streaks | Streaks |

TABLE 1-continued

|  |  | Example 16 | Comparative Example 4 | Comparative Example 5 | Comparative Example 6 |
|---|---|---|---|---|---|
| (200 g scale | 10 minutes | No streaks | Streaks | Streaks | Streaks |
| Homogenizer | 1 minutes | No streaks | Streaks | Streaks | — |
| @ 3000 rpm | 2 minutes | No streaks | Streaks | Streaks | — |
| (200 g scale) | 5 minutes | No streaks | Streaks | Streaks | — |
|  | 10 minutes | No streaks | No streaks | No streaks | — |

In addition, fully extended water based slurry compositions have a relatively stable color, shade, hue, chroma (saturation) or lightness, and can resist a change or shift in color, shade, hue, chroma (saturation) or lightness after applying to skin; resist streaking; resist shade change on skin over time; and resist uneven or irregular spreadability. Thus, fully extended water based slurry compositions can maintain color, shade, hue, chroma (saturation) or lightness consistency when applied to the skin, and appearance of color, shade, hue, chroma (saturation) or lightness typically does not substantially change after initially applying to the skin, or after applying to the skin for a period of time (e.g., 1, 2, 3, 4-6, 6-12, or more hours).

Water based slurry compositions can be produced as set forth herein. The invention therefore provides methods of producing (production, manufacture, preparing) water based slurry compositions.

In one embodiment, a method includes providing a pigment and at least one substrate; contacting the pigment or substrate with a surface-treatment agent to produce a surface-modified pigment or substrate, thereby producing a substrate to which the pigment adheres; and dispersing the pigment and substrate in a water medium. In another embodiment, a method includes providing a pigment and at least one substrate; contacting the pigment or substrate with two surface-treatment agents to produce a surface-modified the pigment or substrate, thereby producing a substrate to which the pigment adheres; dispersing the pigment and substrate in a water medium. In various aspects of multiple (e.g., two, three, four, five, etc., or more) surface-treatment agents, the first and second surface treatment agents are hydrophobic, are hydrophilic, or the first is hydrophobic and the second is hydrophilic. In further various aspects of multiple surface-treatment agents, (e.g., two, three, four, five, etc., or more) surface-treatment agents, the first or second surface treatment agent is any of the surface treatment agents of formulas I to XVI in combination. In additional various aspects of multiple surface-treatment agents, the first of said two surface-treatment agents has a hydrophilic-lipophilic balance of about 10 or higher and contains at least one functional group selected from the group consisting of a carboxyl group or a salt of a carboxyl group, a phosphorous group or a salt of a phosphorous group, a sulfur group or a salt of a sulfur group, and a silane group, the second of said two surface-treatment agents has a hydrophilic-lipophilic balance of about 9 or lower and contains at least one functional group selected from the group consisting of carboxyl group or a salt of a carboxyl group, a phosphorous group or a salt of a phosphorous group, a sulfur group or a salt of a sulfur group, and a silane group, and the difference in the hydrophilic-lipophilic values between the first and the second surface-treatment agents is at least about 5.

In a first exemplary embodiment, a pigment (e.g., deflocculated or deagglomerated pigment) and a substrate are combined to form a mixture. The material is mixed with an aqueous solution (e.g., 50-800% water, based on pigment weight) and dispersed. The mixture may include a plurality of different pigments, the pigments in pre-determined amounts or ratios to provide a desired color, shade, hue, chroma (saturation) or lightness (see, for example, Example 1). A binder, such as an oil (emollient), is optionally added to the slurry (e.g., 1 to 180 parts of oil per 100 parts powder) and dispersed. One or more surface treatment agents is then dispersed into the slurry (e.g., about 0.5 to 400 parts surface-treatment agent per 100 parts powder). A surface treatment agent(s) is chemically immobilized onto the surface of the substrate or pigment. One to two chemical equivalents of a water-soluble salt of a polyvalent metal, such as an alkaline earth metal, calcium, magnesium, aluminum, titanium, zinc, or zirconium sulfate or chloride, may be added to assist in linking the functional group of the surface-treatment agent to the surface of the pigment or substrate material. Following surface treatment, surface-modified substrate or pigment is optionally dehydrated and rinsed to remove any secondary salts and byproducts, if necessary. A filtered cake is thereby produced which may optionally be further dehydrated to be "powder," with less than about 10% loss on drying (LOD), for example, 5% LOD, or 3% LOD. The filtered cake is dispersed into a water phase containing cosmetic ingredients such as water phase thickening agents, preservatives, fragrance, etc., thereby producing a water based slurry composition.

In a second exemplary embodiment, a pigment is mixed with 30% or more (e.g., greater than 40%, 50 to 100%, or at least 70%) based on weight of pigment and any solids present in the slurry) of water and dispersed. An aqueous solution of a second surface-treatment agent, such as a water-soluble alkali metal salt of a fatty acid, is added to the slurry and dispersed. Then 1 to 2 chemical equivalents of a water soluble salt of a polyvalent metal, such as an alkaline earth metal, aluminum, titanium, zinc, stannic, or zirconium sulfate or the like is added. The polyvalent metal will link the lipophilic moiety of the second surface-treatment agent to the surface of the particles of pigment. Next, a first surface-treatment agent, such as a water-soluble alkali metal salt of a sugar acid, is added to the slurry and dispersed. Then 1 to 2 chemical equivalents of a water soluble salt of a polyvalent metal, such as an alkaline earth metal, aluminum, titanium, zinc or zirconium sulfate or the like is added. The polyvalent metal will link the hydrophilic moiety in the first surface-treatment agent to the surface of the particles of pigment. In an alternative embodiment, a first surface-treatment agent is added to the pigment before a second surface-treatment agent. The resultant surface-modified powder in having both lipophilic and hydrophilic properties from a first and second surface treatment agent is dehydrated (e.g., using a filter press) and rinsed with purified water to remove any secondary salts, if desired. A filtered cake with a controlled HLB value is thereby produced which may optionally be further dehydrated to be "powder," (e.g., by baking in an oven for two hours past the point where the cake reaches a temperature of 100° C.) with less than about 10% loss on drying (LOD), for example, 5% LOD, or 3% LOD. The filtered cake is then crushed to produce a workable powder and dispersed into a water phase containing cosmetic ingredients such as water phase thickening agents, preservatives, fragrance, etc., thereby producing a water based slurry composition.

Water based slurry compositions may be included as a component of a cosmetic or makeup product, such as foundations (liquid foundations, hot-pour cream foundations), eye shadows, eyeliners, mascaras, lotions, creams, balms, concealers, blushes, rouges, eyebrow liners, lip sticks, lip liners, nail polishes, and sunscreens. They may also be used in personal care (toiletry) products, such as shampoos, conditioners, lotions, deodorants, antiperspirants, moisturizers, balms, soaps and gels, ointments, salves and creams. When water based slurry compositions are in a cosmetic, makeup or personal care product, other typical components used in cosmetic or toiletry products can be added, if desired.

Water based slurry compositions can be blended together in order to produce a different color, shade, hue, chroma (saturation) or lightness. For example, to adjust or change the color, shade, hue, chroma (saturation) or lightness of a water based slurry composition, a particular color, shade, hue, chroma (saturation) or lightness can be mixed with one or more other powder(s) having a different color, shade, hue, chroma (saturation) or lightness by blending together with a homogenizer. If two or more water based slurry compositions are to be mixed with each other, they may be blended in a mixer to produce a desired color, shade, hue, chroma (saturation) or lightness. Thus, water based slurry compositions of the invention can be adjusted for color, shade, hue, chroma (saturation) or lightness by simple blending without requiring multistep processing, and are therefore more readily formulated or included in cosmetic, makeup, and personal care products.

Water based slurry compositions can be included in containers and kits, optionally including instructions for applying the composition. Specific non-limiting examples of containers and kits include a bottle, vial, jar or tube.

A container or kit optionally includes "packaging material," which refers to a physical structure housing a container or kit, or a component(s) of the container or kit. The packaging material can be made of material commonly used for such purposes. A container or kit can include a label or packaging insert with appropriate instructions, for example. Instructions may be on "printed matter," e.g., on paper or cardboard within the container or kit, or on a label affixed to the container or kit. Instructions may be provided on audio or video medium, such as an a computer readable medium, for example, floppy diskette or hard disk, optical CD such as CD- or DVD-ROM/RAM, magnetic tape, electrical storage media such as RAM and ROM and hybrids of these such as magnetic/optical storage media.

Specific non-limiting examples of containers and kits suitable for water based slurry compositions include bottles, vials, jars, and tubes. Materials suitable for bottles, vials, jars, and tubes include metal, glass or a polyolefin. Exemplary metals include iron (steel) and aluminum. Exemplary polyolefins include polystyrene, polypropylene, polyethylene, and polybutylene. Additional specific non-limiting examples of containers and kits include pouches.

Containers and kits may be sealed. Containers and kits may include multiple (two or more) types of water based slurry compositions. For example, a container can include two or more bottles, each of which contain a different color, shade, hue, chroma (saturation) or lightness of a water based slurry composition. A container may contain each bottle in an individual package.

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

All publications, patents, and other references cited herein are incorporated by reference in their entirety. In case of conflict, the present specification, including definitions, will control.

As used herein, singular forms "a," "and," and "the" include plural referents unless the context clearly indicates otherwise. Thus, for example, reference to "a pigment" includes a plurality of pigments, reference to "a substrate" can include a plurality of substrates and reference to "an extender, oil, emulsifier, emollient, fat, hydrocarbon, surface treatment agent, surfactant, etc." can include a plurality of extenders, oils, emollients, fats, hydrocarbons, surface treatment agents, surfactants, and so forth.

As used herein, all numerical values or numerical ranges include whole integers and fractions thereof within or encompassing such ranges unless the context clearly indicates otherwise. Thus, for example, reference to values such as 0 to 25% include 0% to 5% (i.e., 1, 2, 3, 4, 5%, or 1.1, 1.2, 1.3, 1.4, 1.5%, etc.), 10% to 20% (10, 11, 12, 13, 14%, etc., or 10.1, 10.2, 10.3, 10.4, 10.5, etc.), and so forth; and reference to a range, for example, from about 10 to 18 include 10 to 12, 10 to 13, 10 to 14, 11 to 13, 11 to 14, 11 to 15, 10.1 to 10.3, 10.3 to 10.5, 10.6 to 10.8, etc.

Reference to specific amount of a given ingredient or component in a water based slurry composition (e.g., a pigment, substrate, extender, oil, binder, surface treatment agent, etc.), such as the components and ingredients listed in Example 1, include variations within about 1 to 20%, or 1 to 10%, or 5 to 10%, unless indicated otherwise. The term "about" typically refers to a value with about +/−1 to 10%, or 5 to 10% of the reference value.

As used herein, the term "QS," as is accustomed in the art, means a "sufficient quantity" to obtain the desired functionality. For a fragrance, the functionality is typically obtained using from about 0.05 to 1.0 wt %; for a preservative, the functionality is typically obtained using from about 0.01 to 1.0 wt %.

The invention is generally disclosed herein using affirmative language to describe the numerous embodiments. The invention also specifically includes embodiments in which particular subject matter is excluded, in full or in part. For example, one or more powder materials (e.g., substrates, pigments, pigment extender, etc.), surface treatment agents, binders (e.g., oils), emollients, emulsifiers, fats, fatty acids, hydrocarbons, waxes, paraffins, surface treatment agents, preservatives and fragrances can be specifically excluded in a composition or method of the invention. Thus, even though the invention is generally not expressed herein in terms of what the invention does not include, compositions and methods of the invention include embodiments in which one or more powder materials (e.g., substrates, pigments, extenders, etc.), surface treatment agents, additives or binders (e.g., oils, emollients, emulsifiers, fats, fatty acids, hydrocarbons, waxes, paraffins, etc.), preservatives, fragrances, etc., are excluded.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example includes a description of a water base makeup cosmetic composition.

Water base mousse makeup example 1 (Table 2) was prepared and a sensory test was conducted to compare to the conventional makeup formulas, such as W/S liquid foundation, O/W liquid foundation and anhydrous mousse makeup.

TABLE 2

Water Base Mousse Makeup Example 1

| | |
|---|---|
| Potassium Myristate | 0.75 |
| Sodium Myristoyl Sarcosinate | 0.75 |
| Triethoxy Caprylsilane | 0.75 |
| Talc | 13.30 |
| Red Iron Oxide | 0.12 |
| Yellow Iron Oxide | 0.36 |
| Black Iron Oxide | 0.04 |
| Titanium Dioxide | 2.00 |
| Bismuth Oxychloride | 0.75 |
| Polymethylmethacrylate | 1.00 |
| Boron Nitride | 0.75 |
| Nylon | 0.75 |
| Silica | 0.25 |
| Vegetable Squalane | 1.20 |
| Shea Butter | 0.25 |
| Meadowfoam Seed Oil | 0.50 |
| Pentaerythritol Tetra Ethylhexanoate | 0.75 |
| Sodium Polyacrylate (and) Dimethicone (and) Cyclopentasiloxane (and) Trideceth-6 (and) PEG/PPG-18/18 Dimethicone (DOW CORNING 2051 Fluid) | 2.50 |
| Water | Balance to 100.00 |
| Preservatives | QS |
| Fragrance | QS |

Procedure for Water Base Mousse Makeup—

Powder materials are mixed with 50 to 800% (based on weight of the pigment) water and dispersed. An aqueous solution of one or more surface treatment agents, for instance, a water-soluble alkali metal salt of a fatty acid or an acyl amino acid, is added (0.5 to 400 parts surface treatment agent per 100 parts powder) to the slurry and dispersed. An oil (1 to 180 parts of oil per 100 part powder) is then introduced to the system. Oil addition is optional. One to two chemical equivalents of a water-soluble salt of a polyvalent metal, such as an alkaline earth metal, calcium, magnesium, aluminum, titanium, zinc, or zirconium sulfate or chloride, may be added to assist in linking the functional group of the surface-active agent to the surface of the particles of the powder material. The resultant coated, surface-modified powder material is dehydrated using a filter press and rinsed with purified or de-ionized water to remove any secondary salts and biproducts, as necessary. The filtered cake is dispersed into water phase containing cosmetic ingredients such as water phase thickening agents, preservatives, fragrance and so on.

TABLE 3

Comparative Example 1, O/W liquid foundation

| Phase | Ingredient | Amount |
|---|---|---|
| Phase A | Water | Balance to 100.00 |
| | Glycerin | 4.00 |
| | Butylene Glycol | 3.00 |
| | Xanthan Gum | 0.20 |
| | Triethanolamine | 0.14 |
| | Tetrasodium Ethylenediaminetetraacetate | 0.20 |
| | Sodium Cetearyl Sulfate | 0.80 |
| Phase B | Red iron oxide, Disodium Stearoyl Glutamate | 0.52 |
| | Yellow iron oxide, Disodium Stearoyl Glutamate | 1.60 |
| | Black iron oxide, Disodium Stearoyl Glutamate | 0.18 |
| | Titanium dioxide, Disodium Stearoyl Glutamate | 9.00 |
| | Mica, Disodium Stearoyl Glutamate | 2.00 |
| Phase C | ININ | 4.00 |
| | Shea Butter | 1.00 |
| | Isododecane | 15.00 |
| | Isostearic Acid | 1.20 |
| | Cetearyl Alcohol & Cetearyl Phosphate | 1.00 |
| | Glyceral Stearate & Peg-100 Stearate | 1.50 |
| | Behenyl Alcohol | 0.75 |
| | Phenoxyethanol | 1.00 |

Procedure for O/W Liquid Foundation (Comparative Example 1, Table 3)—

Add phase A to a beaker and mix with a homogenizer until homogeneous. Set aside. Then take phase B and place it in a blender and mix on high for 2 minutes. Check the dispersion and mix again if necessary. Place phase C into a beaker and begin melting waxes on mid heat (30-35° C.). Slowly add oils. Add phase B to phase C and begin homogenizing for about 3 to 5 minutes. Slowly add phase B & C to A and continue homogenizing for 5 minutes once all is incorporated. Let cool and pour into desired container.

TABLE 4

Comparative Example 2, W/S liquid foundation

| Phase | Ingredient | Amount |
|---|---|---|
| Phase A | Water | Balance to 100.00 |
| | Glycerin | 7.00 |
| | Sodium Polyacrylate (and) Dimethicone (and) Cyclopentasiloxane (and) Trideceth-6 (and) Peg/PPG-18/18 Dimethicone | 0.20 |
| | Butylene Glycol | 4.00 |
| Phase B | Red iron oxide, Disodium Stearoyl Glutamate | 0.43 |
| | Yellow Disodium Stearoyl Glutamate iron oxide, | 1.29 |
| | Black iron oxide, Disodium Stearoyl Glutamate | 0.16 |
| | Titanium Dioxide, Disodium Stearoyl Glutamate | 8.00 |
| | Sericite, Disodium Stearoyl Glutamate | 5.00 |
| | Mica, Disodium Stearoyl Glutamate | 6.00 |
| Phase C | BIS-PEG/PPG-14/14 Dimethicone, Cyclopentasiloxane | 4.00 |
| | Shea Butter | 1.00 |
| | Cyclomethicone | 16.35 |
| | Dimethicone | 10.00 |
| | Phenyl Trimethicone | 2.50 |
| | Phenoxyethanol | 1.00 |

Procedure for W/S Liquid Foundation (Comparative Example 2, Table 4)—

Add phase A to a beaker and mix with a homogenizer until homogenious. Set aside. Then take phase B and place it in a blender and mix on high for 2 minutes. Check the dispersion and mix again if necessary. Place phase C into a beaker and begin melting waxes on mid heat (30-35° C.). Slowly add oils. Add phase B to phase C and begin homogenizing for about 3 to 5 minutes. Slowly add phase B & C to A and continue homogenizing for 5 minutes once all is incorporated. Let cool and pour into desired container.

TABLE 5

Comparative Example 3, Anhydrous Mousse Makeup

| Phase A | Red Iron Oxide, Potassium Myristate | 0.60 |
| --- | --- | --- |
| | Yellow Iron Oxide, Potassium Myristate | 1.75 |
| | Black Iron Oxide, Potassium Myristate | 0.25 |
| | Titanium Dioxide, Potassium Myristate | 8.00 |
| | Sericite | 1.00 |
| | Nylon 12 | 12.00 |
| | Starch | 15.00 |
| | Kaolin | 1.00 |
| | Polymethylmethacrylate | 6.65 |
| Phase B | Phenyltrimethicone | 18.00 |
| | Dimethicone | 16.00 |
| | Carnauba Wax | 1.50 |
| | Polyethylene | 3.00 |
| | Beeswax | 1.00 |
| | Isododecane | 13.25 |
| | Phenoxyethanol | 1.00 |

Procedure for Anhydrous Mousse Makeup (Comparative Example 3, Table 5)—

Add phase A to a blender and pulverize for 2 minutes. Continue pulverizing until uniform dispersion. Begin melting wax in phase B @approx. 80° C. Once waxes are melted, add other oil except isododecane. While mixing phase B slowly, add phase A to it. Once all incorporated mix for 5 minutes, start cooling. When the temperature reaches approx. 45° C., add isododecane and continue mixing for another 2 minutes.

Sensory tests were conducted with four formulations, example 1 (Table 2) and the three comparative examples (Tables 3-5) described above. Ten women, aged 30 to 50 years, were recruited for the tests and their comments were examined. The results are summarized in Table 6 with the following standard:

Excellent: 8 and more women say "good"
Good: 6 or 7 women say "good"
Fair: 5 or 6 women say "good"
Poor: 4 or fewer women say "good"

TABLE 6

| | | Comparative Examples (Tables 3-5) | | |
| --- | --- | --- | --- | --- |
| | Example 1 (Table 2) Mousse Makeup Example | Comparative Example 1 W/S Liquid Foundation | Comparative Example 2 O/W Liquid foundation | Comparative Example 3 Anhydrous Foundation |
| Application (ease of extention) | excellent/light & smooth | good, heavy, oily | good/little heavy | fair/heavy, oily |
| Application (play-time) | excellent | fair | good | fair |
| Blendability to the skin | excellent/easy, adjustable | good | good | fair |
| Application Feel | excellent/refreshing | fair/heavy (oily) | good | fair/heavy (oily) |
| Appearance | very natural, thin, good coverage | fair | good | fair |
| Coverage | excellent, natural | good | good | good |
| Wearability | 8 hours | 6 hours | 5 hours | 4 hours |

The "wearability" values in Table 6 in hours are the average hours requiring another foundation application due to color dullness or powder coming off. The greater the number of hours, the more longer the wear.

TABLE 7

Water Base Mousse Eye Shadow Example

| Potassium Myristate | 1.00 |
| --- | --- |
| Disodium Stearoyl Glutamate | 1.00 |
| Triethoxy Caprylsilane | 0.75 |
| Talc | 13.00 |
| Red Iron Oxide | 1.90 |
| Yellow Iron Oxide | 1.90 |
| Black Iron Oxide | 1.90 |
| Mica and Ferric Ferrocyanide | 2.40 |
| Sodium Polyacrylate (and) Dimethicone (and) Cyclopentasiloxane (and) Trideceth-6 (and) PEG/PPG-18/18 Dimethicone (DOW CORNING 2051 Fluid) | 2.40 |
| Water | Balance to 100.00 |
| Preservatives | QS |

The procedure for making water base mousse eye shadow (Table 7) is the same as described above for the "water base mousse makeup example." The "water base mousse eye shadow" contains various kinds of pearl pigments and cosmetic ingredients. The benefits and superior properties of the water base mousse eye shadow are thin application, natural finish, little to no creasing on eye lids, long lasting. In addition, due to superior blendability, it is easy to create a new shade of eye shadow by mixing two or more different shades of eye shadows together.

To further demonstrate the ease and superior blendability and flexibility of water based slurry composition, the following additional examples (Tables 8-10) are illustrated. Water based slurry compositions can be prepared by the procedure described in for water base mousse makeup, Table 2, paragraph [0074].

Table 8: Examples 2-6 have already "thickening" agent
Table 8: Example 7 has no "thickening" agent
Table 9: Examples 8-11 have already "thickening" agent All of these (as is examples 2 to 11, water base slurry compositions) are not wearable because each composition has an extreme shade (too dark, too yellow, too white and too reddish) and or coverage (too much pigment content). These are to be blended and diluted to make wearable cosmetic compositions.

Table 10: Examples 12-15 are water based slurry composition examples

"A disperser" was used as a mixing instrument for blending water base slurry compositions. Approximately 3000 rpm was employed as blending speed. "A disperser" provides more shear than a propeller mixer. Of course, a regular homogenizer can also be used. Even though "gentle agitation" is used for creating target shades, no streaks of colors are observed for water based slurry compositions. It is quick and easy to obtain smooth and uniform texture.

TABLE 8

Slurry Examples The table is based on weight ratio.

|  |  | Example 2 | Example 3 | Example 4 | Example 5 | Example 6 |
|---|---|---|---|---|---|---|
| Treatment agents | Disodium stearoyl glutamate | 0.75 | 0.75 | 0.75 | 0.75 | — |
|  | Potassium palmitate | 0.75 | 0.75 | 0.75 | 0.75 | — |
|  | Potassium myristate | — | — | — | — | 1.50 |
|  | Triethoxy caprylylsilane | 1.00 | 1.00 | 1.00 | 1.00 | — |
|  | Dimethicone | — | — | — | — | 0.25 |
| Pigments | Titanium dioxide | 40.00 | — | — | — | — |
|  | Yellow iron oxide | — | 30.00 | — | — | — |
|  | Red iron oxide | — | — | 40.00 | — | — |
|  | Black iron oxide | — | — | — | 40.00 | — |
| Substrates | Talc | — | — | — | — | 25.00 |
|  | Mica | — | — | — | — | 10.00 |
|  | Sericite | — | — | — | — | 12.50 |
|  | Silica bead | — | — | — | — | 1.00 |
|  | Aluminum potassium silicate | — | — | — | — | 1.50 |
| Thickener | Sodium Polyacrylate (and) Dimethicone (and) Cyclopentasiloxane (and) Trideceth-6 (and) PEG/PPG-18/18 Dimethicone (DOW CORNING 2051 Fluid) | 2.25 | 2.25 | 2.25 | 2.25 | 2.25 |
| Cosmetic Oil | Dimethicone | 1.50 | — | — | — | — |
|  | Cetyl dimethicone | — | — | — | — | — |
|  | Capyl/capric triglyceride | — | 2.50 | 2.50 | 2.50 | — |
|  | Isononyl isononanoate | — | — | — | — | 1.50 |
|  | Dimethicone | — | — | — | — | 0.50 |
|  | Tocopheryl acetate | 0.15 | 0.15 | 0.15 | 0.15 | 0.15 |
|  | Preservatives | QS | QS | QS | QS | QS |
|  | Water | Balance to 100.00 | Balance to 100.00 | Balance to 100.00 | Balance to 100.00 | Balance to 100.00 |

|  |  | Example 7 |
|---|---|---|
| Treatment agents | Sodium myristoyl sarcosinate | 1.00 |
|  | Disodium stearoyl glutamate | — |
|  | Potassium palmitate | — |
|  | Potassium myristate | 0.50 |
|  | Triethoxy caprylylsilane | 3.00 |
|  | Dimethicone | — |
| Pigments | Titanium dioxide | 15.00 |
|  | Yellow iron oxide | 4.00 |
|  | Red iron oxide | 1.20 |
|  | Black iron oxide | 0.75 |
|  |  | 9.00 |
| Substrates | Talc | 9.00 |
|  | Mica | 6.00 |
|  | Sericite | 1.50 |
|  | Kaolin | 1.50 |
|  | Silica bead | 0.50 |
|  | Aluminum potassium silicate | 0.50 |
|  | Ultrafine $TiO_2$ | 6.00 |
|  | Ultrafine ZnO | 12.00 |
| Cosmetic Oil | Isononyl isononanoate | 0.10 |
|  | Tocopheryl acetate | 0.15 |
|  | Octyl methoxycinnamate | 5.00 |
|  | Isododecane | 5.00 |
|  | Preservatives | QS |
|  | Water | Balance to 100.00 |

TABLE 9

Slurry Examples The table is based on weight ratio.

|  |  | Example 8 Blendable "dark" shade | Example 9 Blendable "yellowish" shade | Example 10 Blendable "reddish" shade | Example 11 Blendable "light" shade |
|---|---|---|---|---|---|
| Treatment agents | Sodium myristoyl sarcosinate | 0.50 | 0.50 | 0.50 | 0.50 |
|  | Disodium stearoyl glutamate | — | — | — | — |
|  | Potassium palmitate | 0.75 | 0.75 | 0.75 | 0.75 |
|  | Potassium myristate | — | — | — | — |
|  | Triethoxy caprylylsilane | 1.50 | 1.50 | 1.50 | 1.50 |
| Pigments | Titanium dioxide | 0.50 | 0.50 | 0.50 | 10.00 |
|  | Yellow iron oxide | 4.25 | 8.00 | 2.70 | 0.20 |
|  | Red iron oxide | 5.00 | 0.80 | 6.00 | 0.10 |
|  | Black iron oxide | 12.00 | 0.30 | 0.35 | 0.05 |
| Substrates | Talc | 8.00 | 8.00 | 8.00 | 8.00 |
|  | Mica | 10.00 | 10.00 | 10.00 | 10.00 |
|  | Sericite | 14.00 | 14.00 | 14.00 | 14.00 |
|  | Silica bead | 0.50 | 0.50 | 0.50 | 0.50 |
|  | Aluminum potassium silicate | 0.50 | 0.50 | 0.50 | 0.50 |
| Cosmetic Oil | Cetyl octanoate | 0.50 | 0.50 | 0.50 | 0.50 |
|  | Sodium Polyacrylate (and) Dimethicone (and) Cyclopentasiloxane (and) Trideceth-6 (and) PEG/PPG-18/18 Dimethicone (DOW CORNING 2051 Fluid) | 2.50 | 2.50 | 2.50 | 2.50 |
|  | Capyl/capric triglyceride | 0.50 | 0.50 | 0.50 | 0.50 |
|  | Tocopheryl acetate | 0.10 | 0.10 | 0.10 | 0.10 |
|  | Preservatives | QS | QS | QS | QS |
|  | Water | Balance to 100.00 | Balance to 100.00 | Balance to 100.00 | Balance to 100.00 |

Water base foundations (mousse type) can be prepared using the examples from 2 to 11.

TABLE 10

Blend/Dilution Examples The table is based on weight ratio.

|  |  | Example 12 | Example 13 | Example 14 | Example 15 |
|---|---|---|---|---|---|
| Surface treated powder water slurry | Example 2 | 12.00 | — | — | — |
|  | Example 3 | 5.00 | — | — | — |
|  | Example 4 | 1.00 | — | — | — |
|  | Example 5 | 0.50 | — | — | — |
|  | Example 6 | 30.00 | — | — | — |
|  | Example 7 | — | 30.00 | — | — |
|  | Example 8 | — | — | 45.00 | 1.50 |
|  | Example 9 | — | — | 2.50 | 3.50 |
|  | Example 10 | — | — | 2.50 | 5.15 |
|  | Example 11 | — | — | 1.25 | 41.00 |
| Thickener | Sodium Polyacrylate (and) Dimethicone (and) Cyclopentasiloxane (and) Trideceth-6 (and) PEG/PPG-18/18 Dimethicone (DOW CORNING 2051 Fluid) | 0.75 | 2.50 | — | — |

TABLE 10-continued

Blend/Dilution Examples The table is based on weight ratio.

| | | Example 12 | Example 13 | Example 14 | Example 15 |
|---|---|---|---|---|---|
| Water soluble materials | Plant extracts (polyols base) | 2.00 | — | 1.00 | 1.50 |
| | Sodium ascorbyl phophate | 2.50 | — | — | 1.50 |
| | Magnesium ascorbyl phosphate | — | 3.00 | 1.50 | — |
| | Butylene glycol | 2.00 | — | — | — |
| | Pentylene glycol | — | 3.00 | — | — |
| | Preservatives | QS | QS | QS | QS |
| | Water | Balance to 100.00 | Balance to 100.00 | Balance to 100.00 | Balance to 100.00 |

What is claimed is:

1. A water-based cake material, said cake material comprising pigment and substrate with a moisture content of between 30% and 70%, wherein the pigment and/or substrate has a surface that has been chemically immobilized with at least two surface-treatment agents by mixing a pigment and/or substrate powder together and contacting the powder with at least two different surface-treatment agents, wherein each of the at least two surface treatment agents is selected from a different one of the group consisting of Formulas VIII, X, and XV

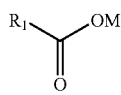

[Formula VIII]

wherein, $R_1$ is an alkyl, alkenyl, alkynyl, alkoxy, aryl, cycloalkyl, arylalkyl group, all of which may be substituted by at least one or more hydroxy group, and may further be substituted by one or more hydroxy, alkoxyl, carboxyl, or oxo group;

$R_1$ is 8 to 24 carbons (C8~C24); and

M is metal or its equivalent;

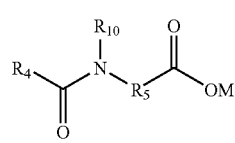

[Formula X]

acylamino acids and their salts, wherein, $R_4$ and $R_5$ are each independently alkyl, alkylamide, alkenyl, alkynyl, alkoxy, aryl, cycloalkyl, arylalkyl, amino acid group, all of which may be substituted by one or more hydroxy group, and may further be substituted by one or more alkoxyl, carboxyl, or oxo group;

$R_4$ is 8 to 24 carbons (C8~C24);

$R_{10}$ is hydrogen or methyl; and

M is hydrogen, or metal or its equivalent;

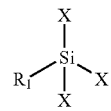

[Formula XV]

wherein, $R_1$ is an alkyl, alkylamide, alkenyl, alkynyl, alkoxy, aryl, cycloalkyl, arylalkyl group, all of which may be substituted by one or more hydroxy group, and may further be substituted by one or more alkoxyl, carboxyl, or oxo group;

or $R_1$ is 8 to 24 carbons (C8~C24); and

X is an alkoxy or a halogen.

2. The cake material of claim 1, wherein at least three surface-treatment agents are used and are selected from: (1) a metal salt of myristate or palmitate; (2) a metal salt of stearoyl glutamate or myristoyl sarcosinate; and (3) a caprylylsilane.

3. The water-based cake material of claim 1, wherein the surface treatment agents are hydrophobic or hydrophilic.

4. The water-based cake material of claim 1, wherein the pigment is substantially deagglomerated or defloculated.

5. The water-based cake material of claim 1, wherein the pigment comprises two or more different pigments, and wherein each pigment adheres to the substrate.

6. The water-based cake material of claim 1, wherein the pigment comprises three, four, five or more different pigments, and wherein each pigment adheres to the substrate.

7. The water-based cake material of claim 1, wherein each pigment has a different color, shade, hue, chroma (saturation) or lightness.

8. The water-based cake material of claim 1, wherein the pigment is selected from the group consisting of titanium dioxide, zinc oxide, zirconium oxide, zirconium dioxide, iron oxide, ultramarine, pearl pigment, manganese violet, Prussian blue, chromium oxide, chromium hydroxides, and mixtures thereof.

9. The water-based cake material of claim 1, wherein the pigment is selected from the group consisting of rutile, anatase, ultrafine $TiO_2$, ultrafine ZnO, yellow iron oxide, red iron oxide, brown iron oxide, black iron oxide, ultramarine blue, ultramarine violet, ultramarine pink, mica, titanated mica, and mixtures thereof.

10. The water-based cake material of claim 1, wherein the substrate is selected from the group consisting of clay, mica, timron super silver, a mica coated with titanium dioxide, talc, kaolin, sericite, silica, aluminum silicate, magnesium silicate, calcium sodium silicate, fumed silica, alumino-silicate, a mineral, nylon, boron nitride, an acrylate, polymethyl methacrylate (PMMA), a metal powder, ceramic powder, cotton powder, cellulose, urethane, styrene, polyolefin, polyetheylene, polyamide, zirconium, starch and starch derivatives such as aluminum starch octenylsuccinate, calcium carbonate (chalk), and mixtures thereof.

11. The water-based cake material of claim 1, wherein the surface-treatment agents are present in an amount of from about 1% to 15% by weight of the cake material.

12. The water-based cake material of claim 1, wherein the amount of pigment is less than about 70% by weight of the cake material.

13. The water-based cake material of claim 1, wherein the pigment is substantially uniformly distributed onto the surface of the substrate.

* * * * *